United States Patent [19]
Saxena et al.

[11] Patent Number: 5,462,659
[45] Date of Patent: Oct. 31, 1995

[54] CHROMATOGRAPHY COLUMN

[75] Inventors: Vinit Saxena, Pleasanton; Paul Young, Walnut Creek, both of Calif.

[73] Assignee: Sepragen Corporation, San Leandro, Calif.

[21] Appl. No.: 77,427

[22] Filed: Jun. 15, 1993

[51] Int. Cl.⁶ ................................................... B01D 15/08
[52] U.S. Cl. .................... 210/198.2; 96/106; 210/238; 210/656; 422/70
[58] Field of Search ............... 73/61.52, 61.53; 96/101, 106; 210/96.1, 198.2, 232, 237, 238, 656, 635; 422/70

[56] References Cited

U.S. PATENT DOCUMENTS

| | | | |
|---|---|---|---|
| 2,708,519 | 5/1955 | Novak | 210/198.2 |
| 4,582,608 | 4/1986 | Ritacco | 210/656 |
| 4,627,918 | 12/1986 | Saxena | 210/198.2 |
| 4,737,292 | 4/1988 | Ritacco et al. | 210/656 |
| 4,840,730 | 6/1989 | Saxena | 210/96.1 |
| 5,021,162 | 6/1991 | Sakamoto et al. | 210/198.2 |
| 5,192,433 | 3/1993 | Shalon | 210/198.2 |
| 5,282,973 | 2/1994 | Mann | 210/198.2 |
| 5,324,426 | 6/1994 | Joseph et al. | 210/656 |
| 5,366,621 | 11/1994 | Bidell et al. | 210/656 |

FOREIGN PATENT DOCUMENTS

| | | | |
|---|---|---|---|
| 330633 | 8/1989 | European Pat. Off. | 96/101 |

*Primary Examiner*—Joseph W. Drodge
*Attorney, Agent, or Firm*—Shyamala T. Rajender

[57] ABSTRACT

An improved axial flow chromatography column for separations dependent upon bed depth, such as size exclusion and where changes of column volume necessitate bed height adjustments. The improvements include a snap-action lever or a collet arrangement which permits quick and easy movement of the bed adjuster; a flush seal assembly at the outlet frit and a V-shaped seal in the bed adjuster which obviates dead volume gap of conventional O-ring seals; lens-shaped frits convex on the inlet and outlet sides provide for uniform flow through the column, and the access ports eliminate the contamination problem by providing easy access for cleaning and aspiration of liquid; and a combined inlet tube and adjuster tube assembly eliminates the need for threaded components which make sanitation difficult.

24 Claims, 10 Drawing Sheets

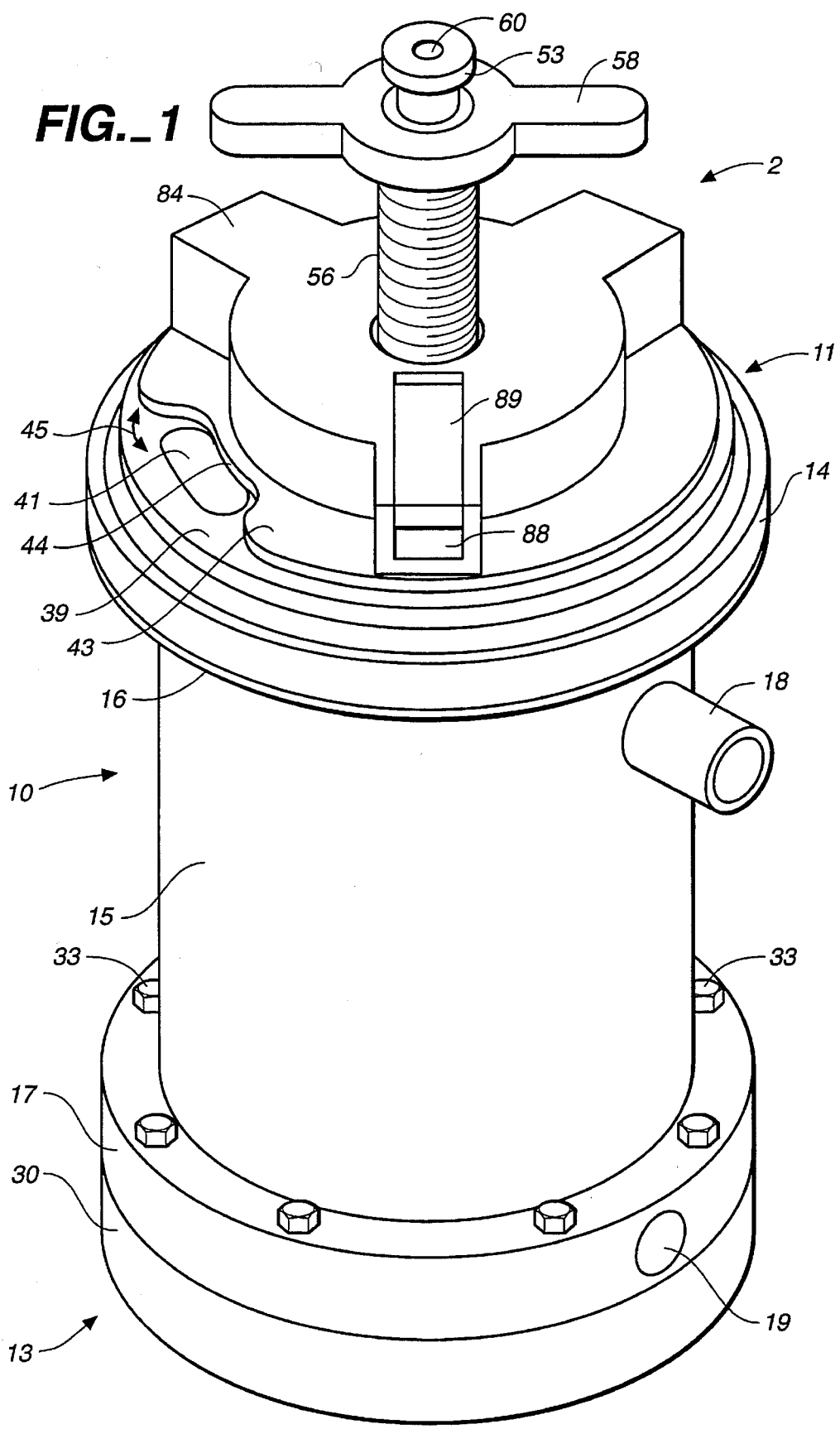
FIG._1

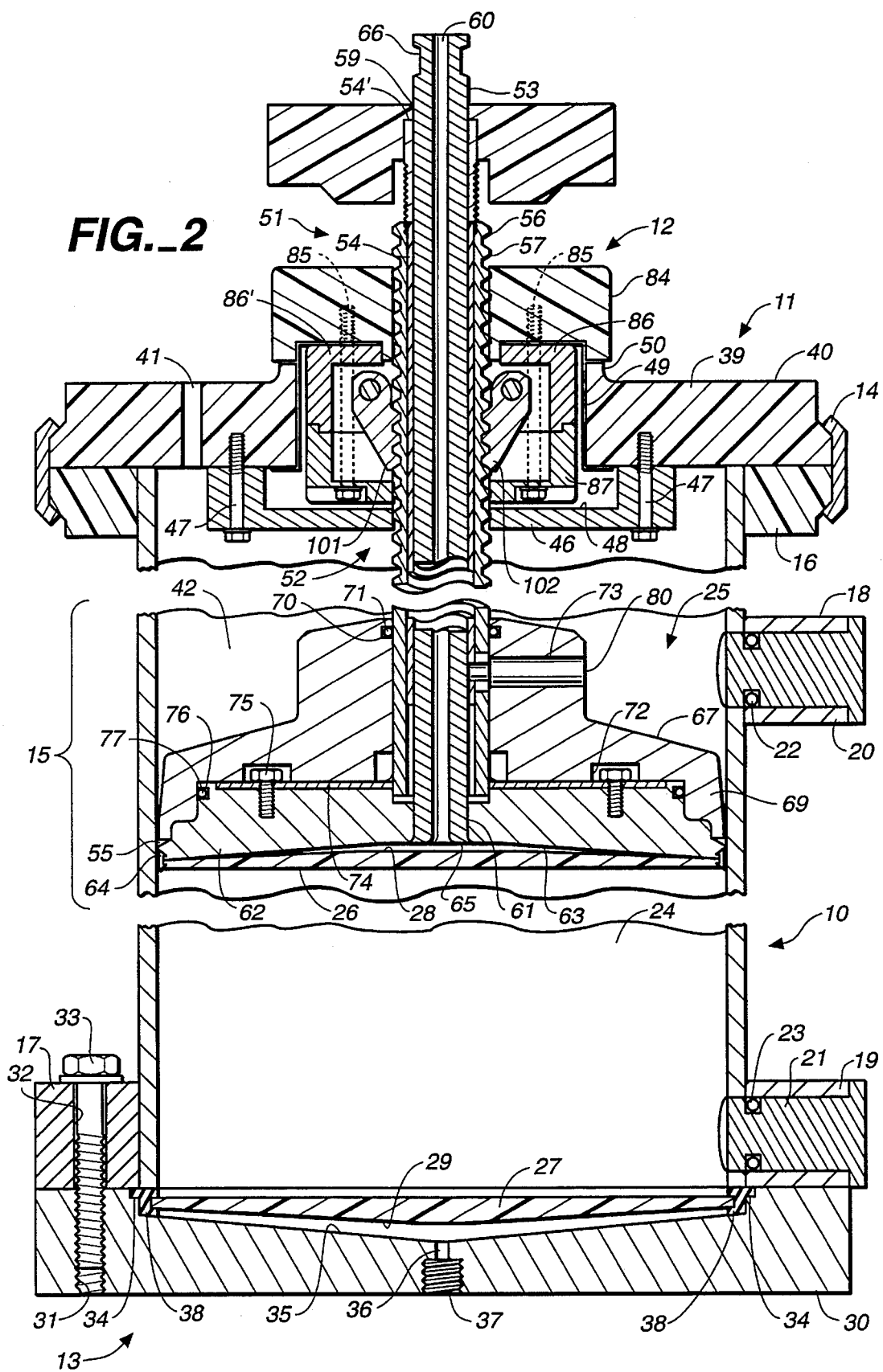
FIG._2

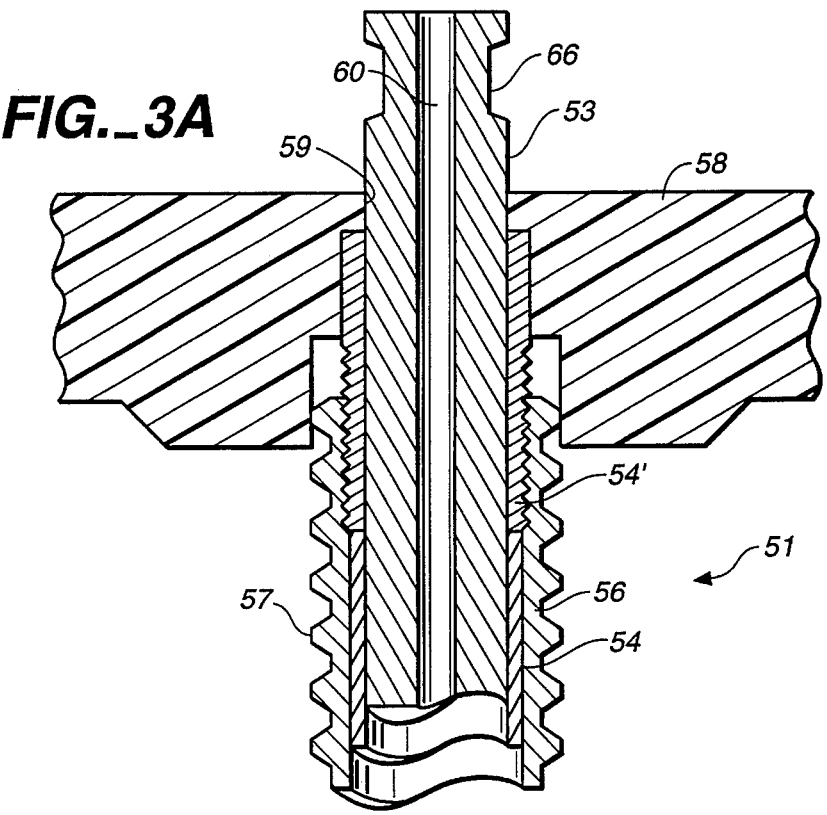
FIG._3A
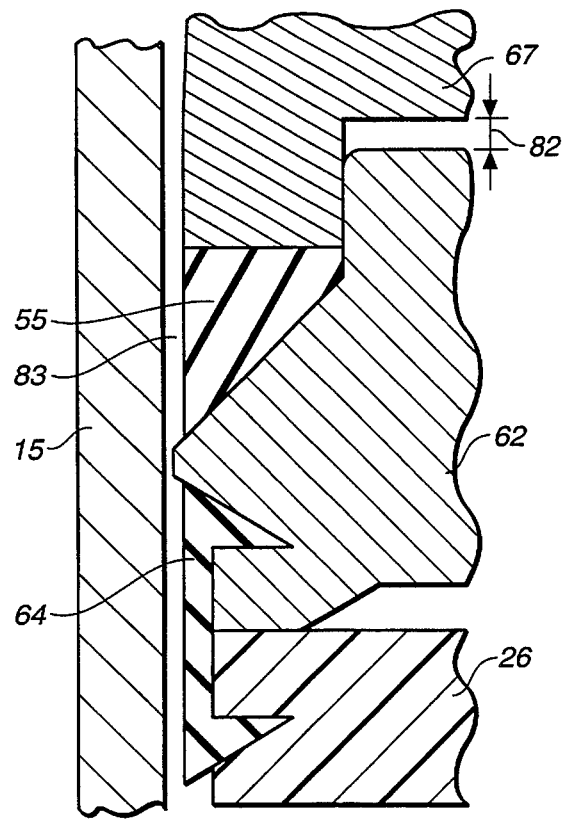
FIG._4A
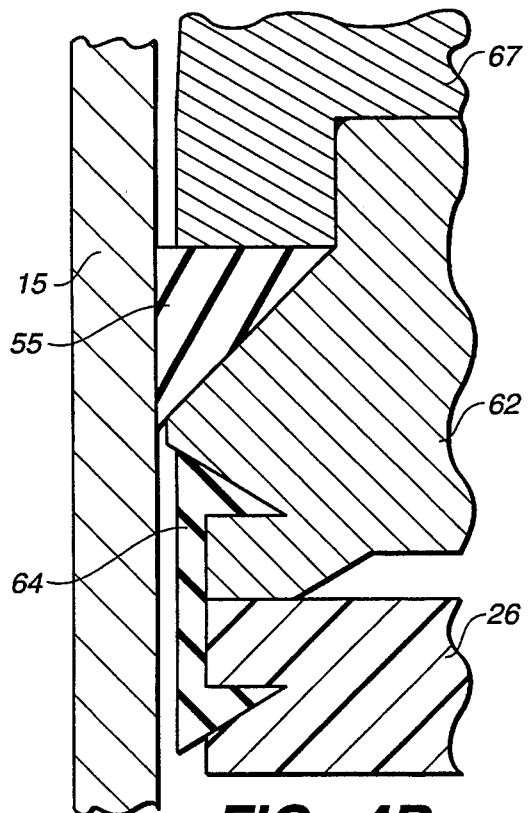
FIG._4B

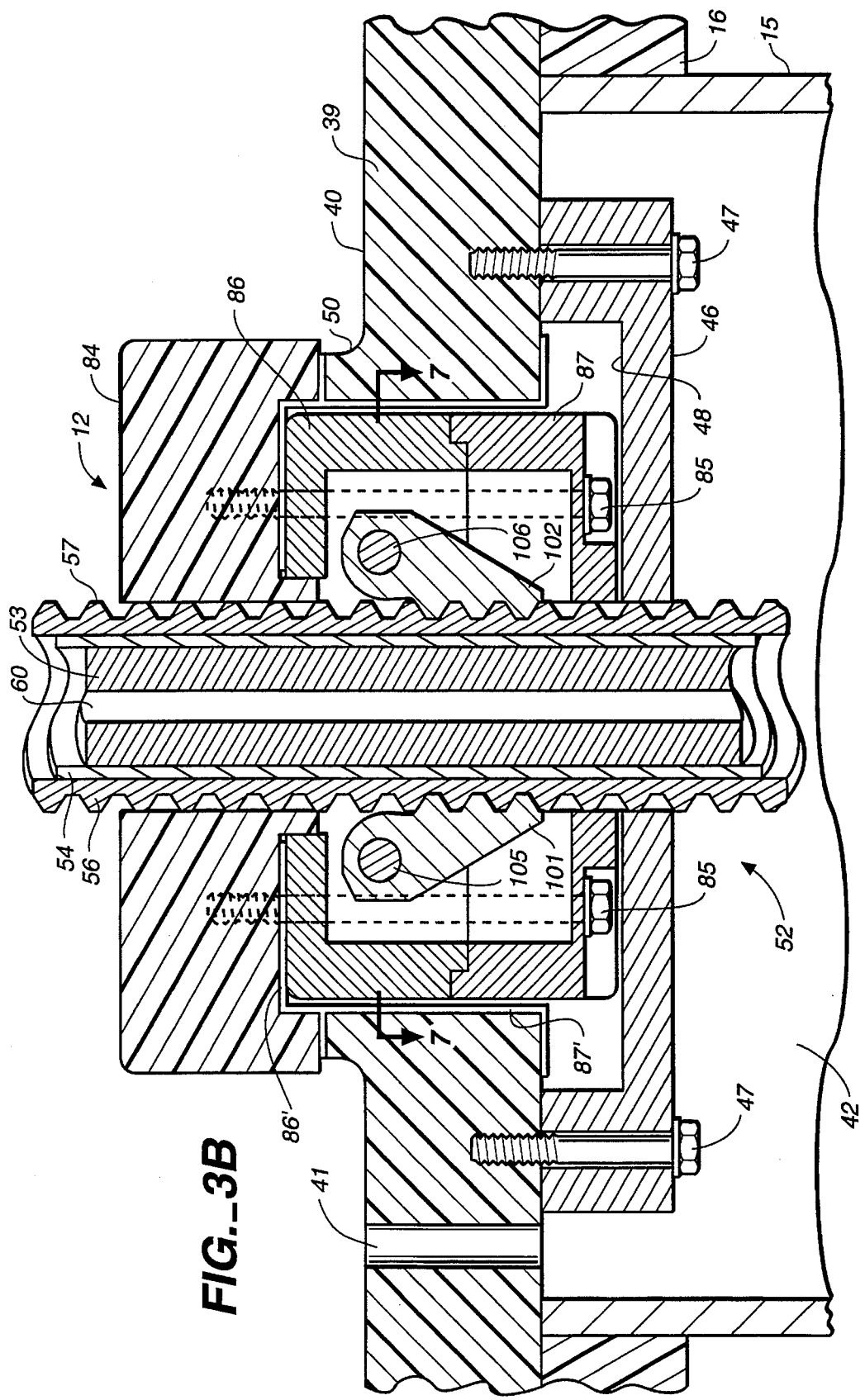
FIG._3B

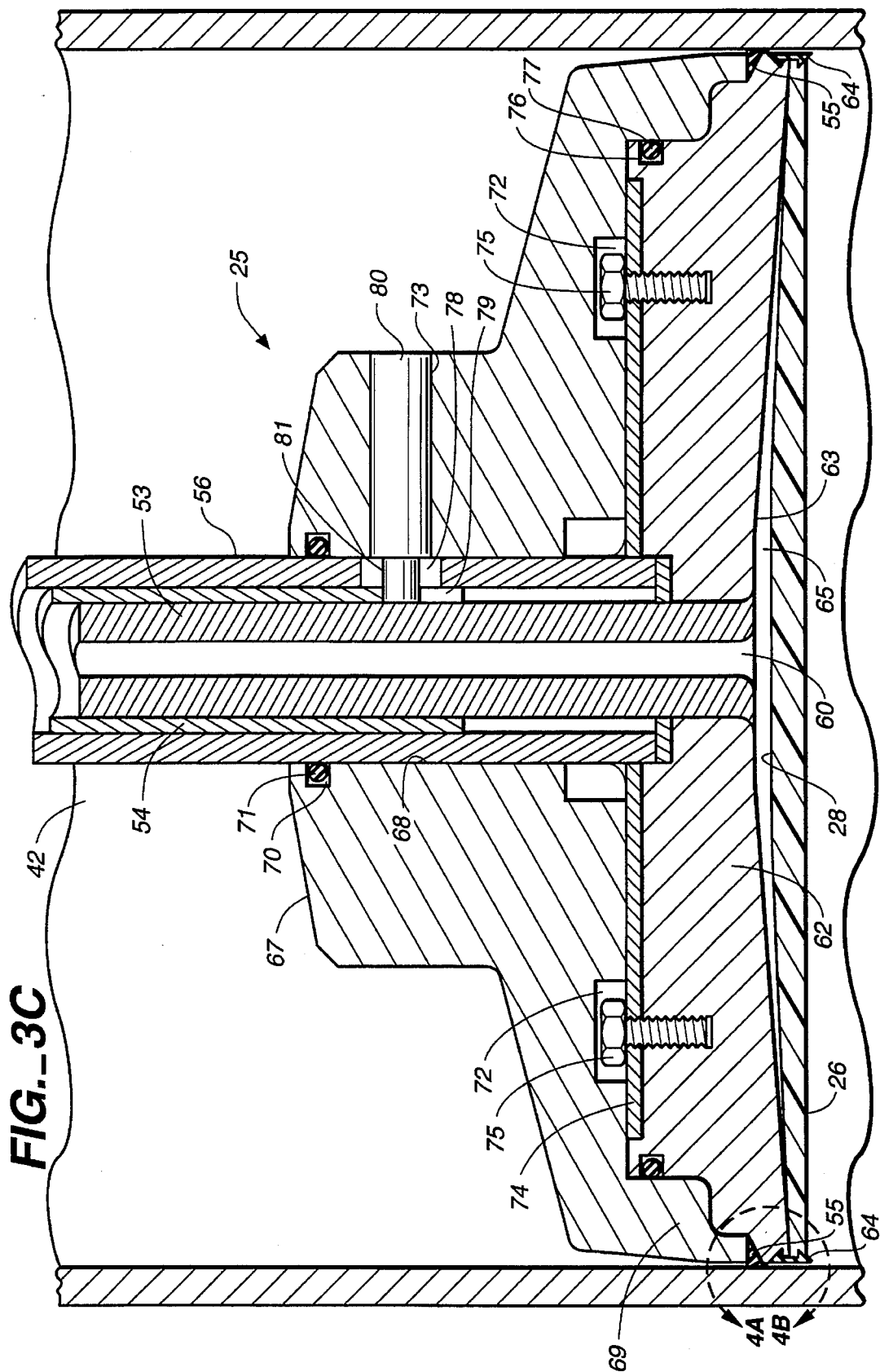
FIG._3C

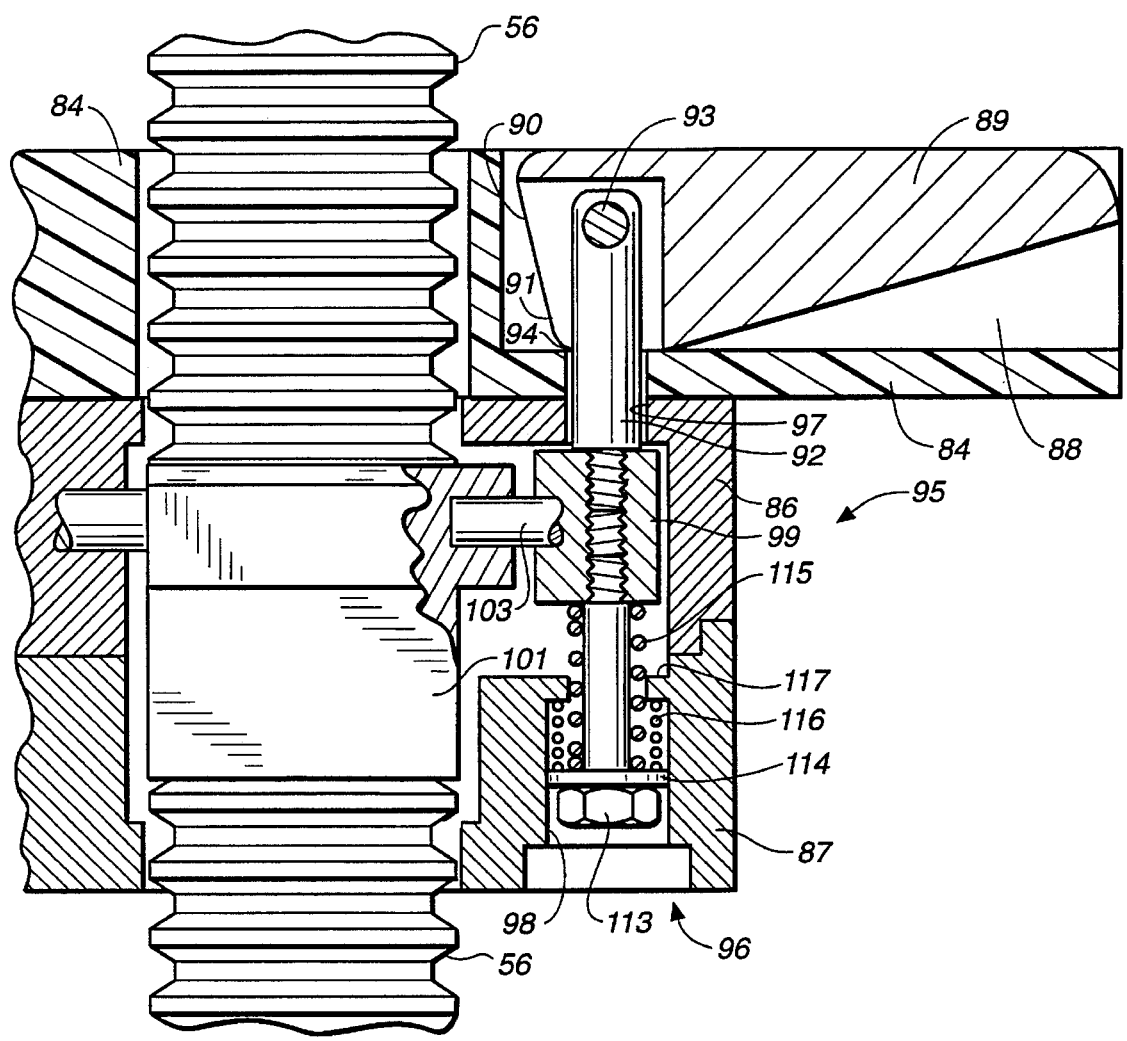
FIG._5A

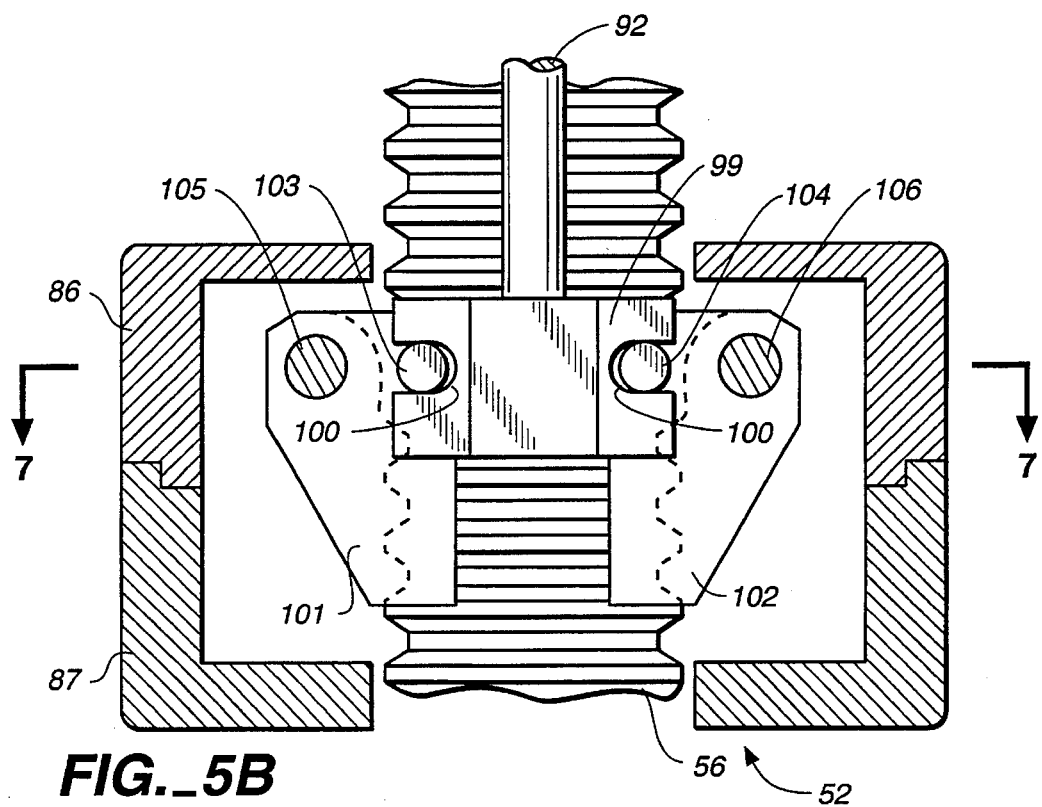
FIG._5B
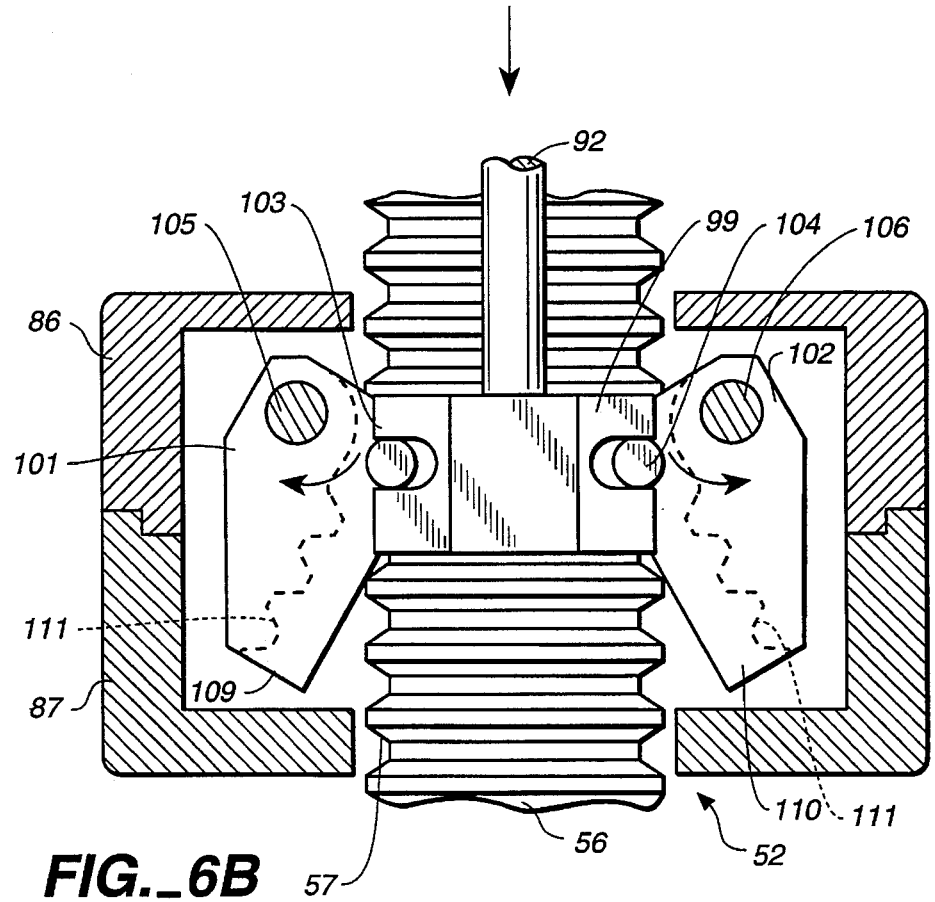
FIG._6B

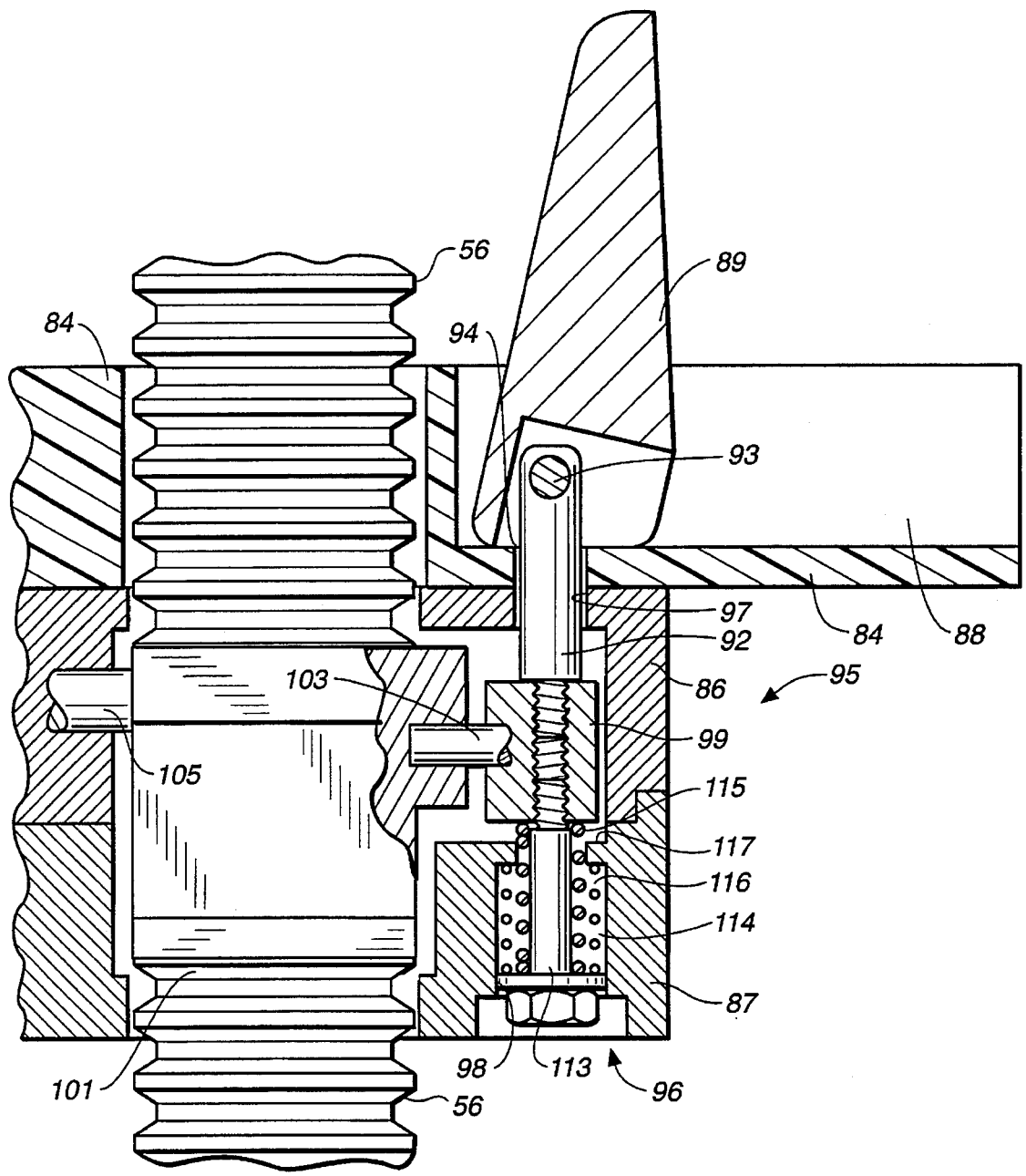
FIG._6A

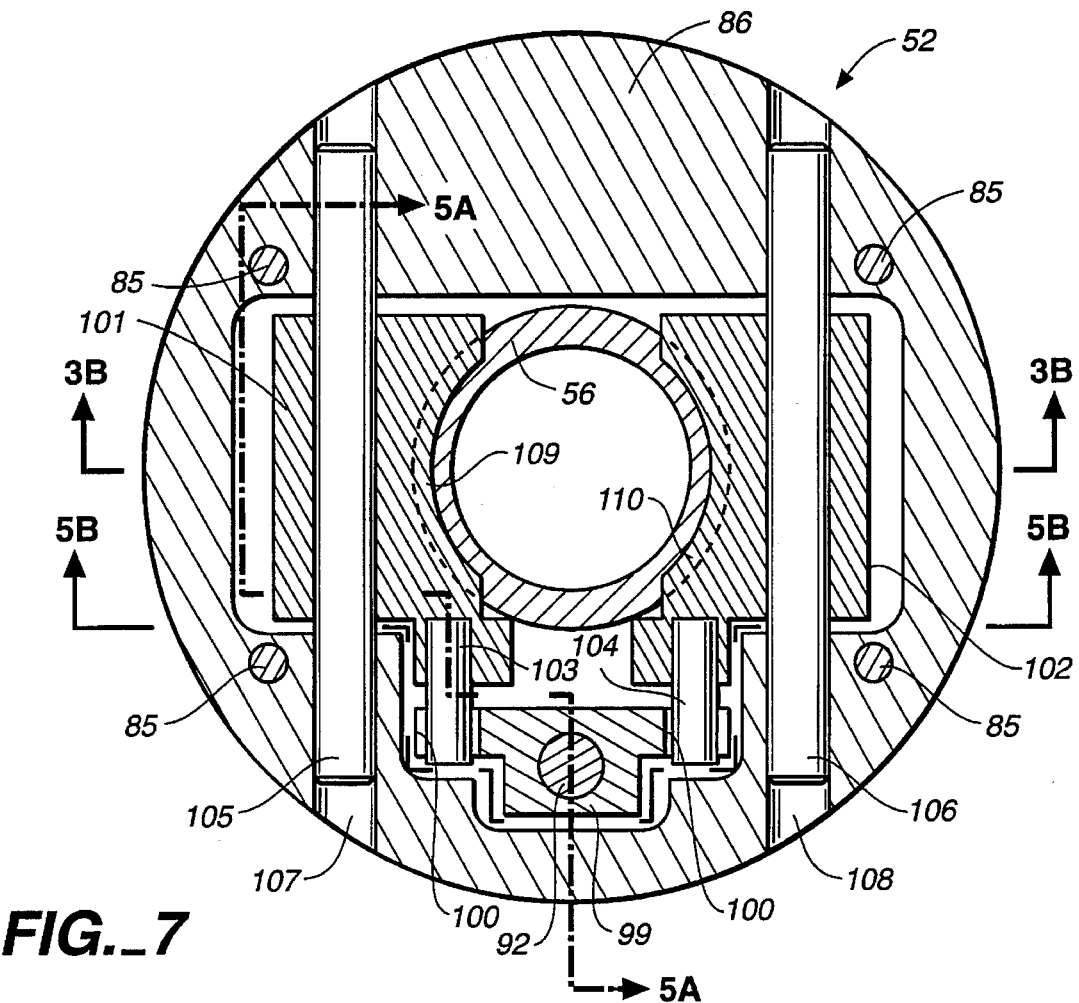
FIG._7
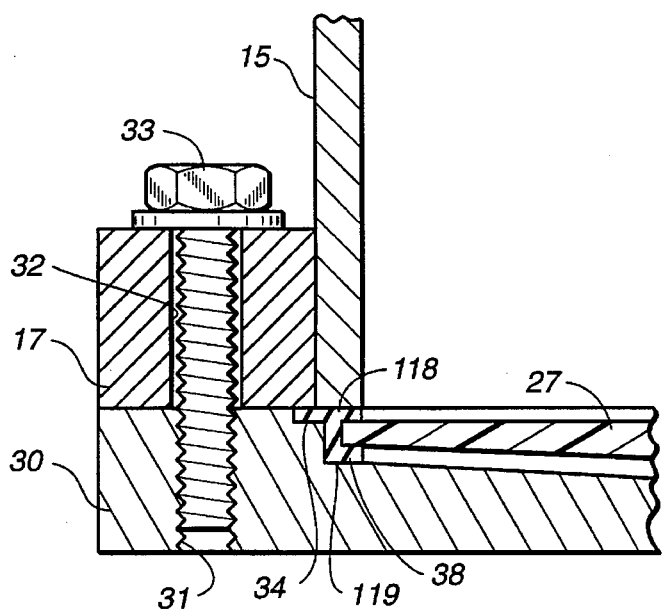
FIG._8

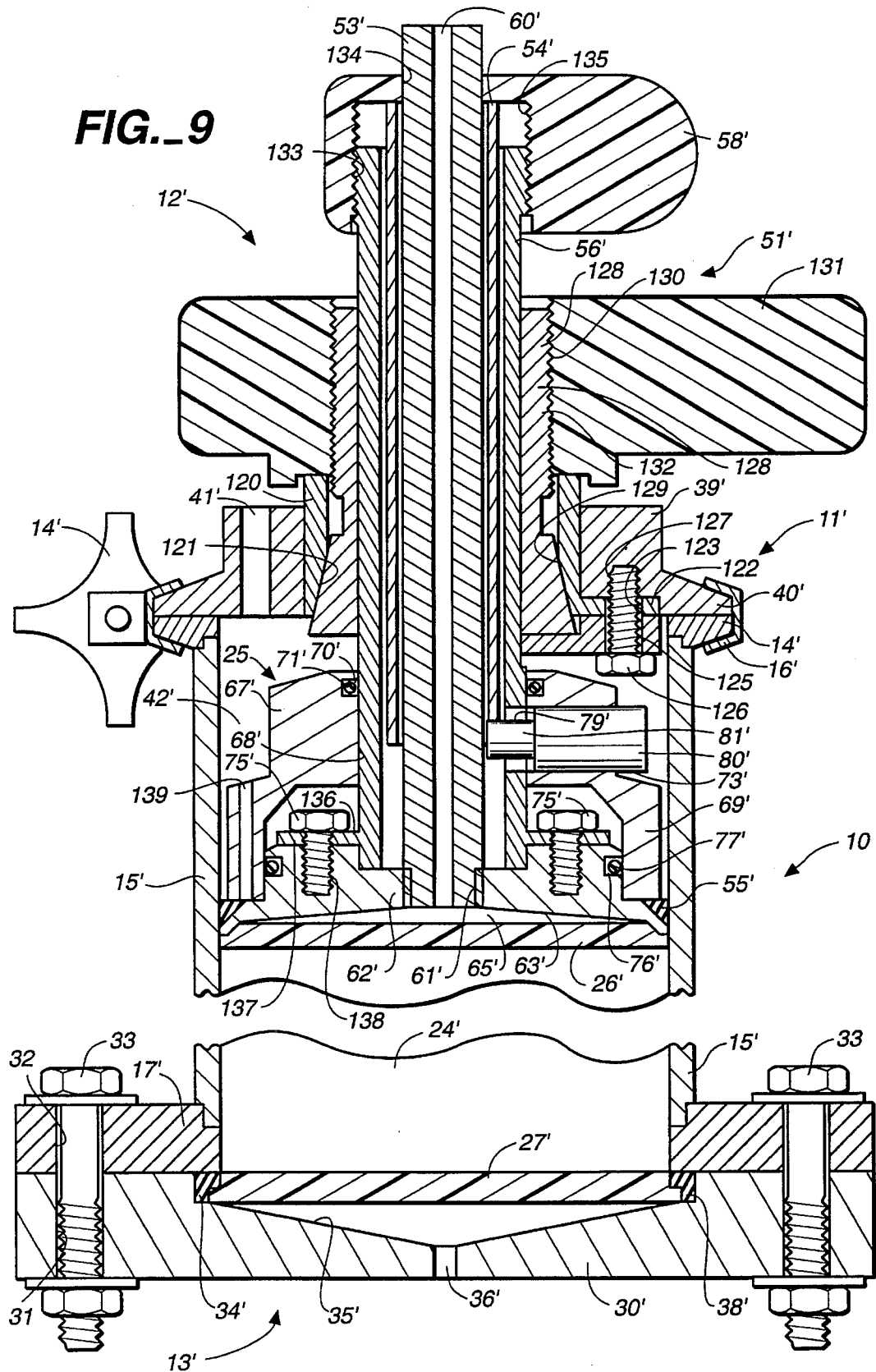
FIG._9

CHROMATOGRAPHY COLUMN

BACKGROUND OF THE INVENTION

The present invention relates to axial flow chromatography columns, particularly to adjustable bed axial flow columns, and more particularly to an improved axial flow column which allows for quick bed adjustment, minimizes dead volume gap, utilizes lens-shaped frits, and provides easy access for cleaning and packing the column.

Chromatography is a term applied to a wide variety of separation techniques based upon the sample interchange between a moving phase, which can be a gas or liquid, and a solid stationary phase. When gas is the moving er mobile phase, the technique is termed gas chromatography and when liquid is the moving or mobile phase, the technique is termed liquid chromatography.

Separation techniques are generally classified into either analytical or preparative depending on the objective. In analytical separations, the objective is high resolution separation, identification and quantification of the various components of a sample mixture. In preparative chromatography the objective is the isolation of pure quantities of the constituents in the sample.

Such separation techniques include liquid absorption chromatography used for organic and biochemical analysis; ion exchange chromatography used for separation of ionic species; affinity chromatography based on the attraction of a ligand for a given component of the sample bonded to the solid stationary phase; and liquid-liquid or partition chromatography which involves the use of a thin layer of the sample dissolved in an appropriate solvent liquid held in place on the surface of a porous inert solid serving as the stationary phase.

In the chromatographic process, it is customary to pass a mixture of the components to be resolved in a carrier fluid through a chromatographic column or apparatus which includes a separation or resolving zone, such as a stationary phase which generally consists of a material or medium which has an active absorptive function for separating or isolating the components in the carrier fluid. The separation or resolving zone usually takes the form of a column, either axial flow or radial flow type, through which the carrier fluid passes. A major problem with the use of prior art axial flow chromatographic columns is the difficulty encountered in obtaining a uniform fluid flow across the column and through the separation medium. Numerous prior types of columns, media or separation bed arrangements, have been developed to provide effective separation of the various components of a sample solution as a carrier fluid is directed through the medium in the column. These prior efforts, dealing with axial flow type columns, are exemplified in U.S. Pat. Nos. 3,422,605 issued Jan. 21, 1969 to R.P. Crowley; No. 3,453,811 issued Jul. 8, 1969 to R.P. Crowley; No. 3,780,866 issued Dec. 25, 1973 to L.V. Ek et al; No. 3,856,681 issued Dec. 24, 1974 to C.N. Huber; No. 4,116,046 issued Sep. 26, 1978 to S. Stein; and No. 4,496,461 issued Jan. 29, 1985 to G. Leeke et al.

While there have been significant advancements in the field of chromatography, there is still a need for the optimization of chromatographic performance by the elimination or minimization of dead volumes in the columns, improving flow through the columns, providing for easy packing and unpacking of the separation medium, reducing contamination and improving sanitation, as well as providing means for easy adjustment of the bed of the columns. The present invention is directed to providing such optimization by utilizing V-ring seals, lens-shaped bed support frits, one-piece construction of the inlet tube and adjuster head, easy access for cleaning, and a snap-action locking lever for rapid movement of the bed adapter.

SUMMARY OF THE INVENTION

It is, thus, an object of the invention to provide an improved preparative chromatography column.

It is a further object of the invention to provide a chromatography column with an arrangement of seals, which minimizes dead volumes therein.

A further object to the invention is to provide bed support frits which promote even sarapie distribution and reduce uneven parabolic sample profile.

Another object of the invention is to utilize materials in the column components which are compatible with chemical sanitation procedures and to construct the components so as to allow for easy and complete sanitation in place, without disassembly of the column.

Yet another object of the invention is to provide a chromatography column which includes at least one access hole for removal or loading of a buffer solution.

Still another object of the invention is to provide a chromatography column with packing and unpacking ports for the separation medium which allow for packing and unpacking the column without removal of the height adjuster assembly.

Yet another object of the invention is to ensure the effectiveness of sanitation of the column and the medium by the elimination of wetted threaded fittings and by the use of a one-piece construction of the inlet tube and adjuster head.

Another object of the invention is to provide rapid movement of the bell adapter via a snap-action locking lever thereon, and to provide for fine adjustments of the bed adapter by a single rotational control handle.

Another object of the invention is to simplify packing and unpacking of the column by use of a quick release band clamp for the column top.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objectives and in accordance with the purpose and principles of the invention as set forth herein, the present invention basically involves an improved preparative axial-flow chromatography column which is constructed so as:

- to eliminate or minimize dead volume therein by improved seal designs on the bed adapter located adjacent to the outlet;
- to improve sample distribution by the use of lens-shaped, convex bed support frits on the inlet and outlet sides;
- to improve sanitation by a one-piece construction of certain components thereby eliminating threaded fittings;
- to provide easy access to the interior of the column to enable complete sanitation without disassembly thereof;

to enable easy column set up and handling by the use of a snap-action locking lever which permits rapid movement of the bed adapter; and to provide easier packing and unpacking of the column by use of a quick release band clamp for securing column components.

BRIEF DESCRIPTION OF THE DRAWINGS

The accompanying drawings, which are incorporated into and form a part of the disclosure, illustrate embodiments of the invention and, together with, the description, serve to explain the principles of the invention.

FIG. 1 is a perspective view of an embodiment of a large chromatography column made in accordance with the present invention;

FIG. 2 is a cross-sectional view of the column illustrated in FIG. 1;

FIGS. 3A–3C constitute an enlarged view of the adjuster assembly of the column of FIGS. 1 and 2;

FIGS. 4A and 4B are enlarged partial views of the seal assembly taken along line 4A–4B of FIG. 3C shown in retracted and compressed positions;

FIGS. 5A and 5B illustrate sections of the snap-action lever mechanism of the FIGS. 1–2 apparatus in its activated/locked position;

FIGS. 6A and 6B illustrate sections of the snap-action lever mechanism of FIGS. 5A–5B in its inactivated/unlocked position;

FIG. 7 is a view taken along the line 7—7 of FIG. 3B illustrating further details of the snap-action lever mechanism;

FIG. 8 is an enlarged view of a portion of the lower frit seals illustrated in FIG. 2; and FIG. 9 is a cross-sectional view of another embodiment of the invention for small applications utilizing similar components of the column illustrated in FIG. 1.

DETAILED DESCRIPTION OF THE INVENTION

The present invention is directed to an improved column for preparative or analytical chromatography which is particularly applicable for separations dependent upon bed depth, such as size exclusion and those processes where changes of volume necessitate bed height adjustments. The improved column of this invention utilizes a simple snap-action lever which permits the bed adjuster to be moved quickly and easily for coarse adjustment. Fine adjustments are made with a single rotational control. Dead volume has been minimized by the seal at the outlet frit being virtually flush with the column wall, thereby preventing a void, which could result in sample mixing during elution, and by the bed adjuster utilizing a V-shaped or triangular seal which obviates the dead volume gap encountered in conventional O-ring seals. In order to counteract the tendency of a sample to descend in an asymmetric parabolic profile, lens-shaped frits are utilized which are thicker in the center on the inlet and outlet sides, and which promote symmetrical sample flow through the bed.

The improved column is also designed to facilitate chemical sanitation of the column components. Not only are the materials of the various components compatible with sanitizing liquids, but the physical construction of the column permits complete access to all wetted parts. Conventional column designs permit accumulation of inaccessible liquid above the bed adjuster seal, leading to the potential for column contamination. The column of this invention eliminates this problem by providing access for cleaning and aspiration of liquid above the bed adjuster. Furthermore, inlet and outlet fittings which are easily cleanable and/or sterilizable are utilized. In addition, the inlet tube and adjuster head are of a one-piece construction, thereby eliminating the need for threaded components that make sanitation difficult.

Packing and unpacking of the bed are also rendered easier by providing packing and unpacking ports in the column housing and by securing the column top to the body with a quick release band clamp. Thus, the improved column of this invention provides for optimization of chromatographic performance. Two embodiments of the column of this invention are illustrated (FIGS. 1–8), one for large column or volume applications and a second (FIG. 9) for small column or volume applications.

Referring now to the drawings, FIGS. 1 and 2 illustrate an embodiment of a large chromatography column which basically consists of a body or housing assembly generally indicated at 10, a top head assembly generally indicated at 11, an adjuster assembly generally indicated at 12, and an outlet head assembly generally indicated at 13, with adjuster assembly 12 being mounted in top head assembly 11 and extending into body assembly 10. Top head assembly 11 is removably connected to body assembly 10 via a quick release band clamp 14.

Body or housing assembly 10 comprises a cylindrical member or body 15, constructed of glass, plastic, etc., with an upper flange 16 having a tapered outer section, and a lower flange 17 secured to or made integral with body 15.

Cylindrical body 15 is provided with a plurality of packing ports 18, only one being shown, located in an upper section thereof, and lower flange 17 is provided with a plurality of unpacking ports 19, only one being shown, with ports 18 and 19 each having a removable plug 20 and 21 therein which includes an O-ring 22 and 23 located at the inner end of plugs 20 and 21 (see FIG. 2). The plugs 20 and 21 may be threaded or friction secured in ports 18 and 19 and inserted so as to be flush with the inner surface of cylindrical body 15.

The packing and unpacking ports 18 and 19 allow for packing and unpacking of the column (body 15) with appropriate separation or packing medium 24 without removing the adjuster assembly 12, which includes a seal/frit activator assembly generally indicated at 25, from the body assembly 10. This provides a significant advantage in the case of large columns where the adjuster assembly is too heavy to lift manually, but can be moved to the upper end of the cylindrical body 15, as described hereinafter, without removal therefrom, such that the medium 24 can be packed and unpacked between an upper or inlet frie 26 and a lower or output or outlet frit 27.

To pack the column (body 15) the unpacking ports 19 are plugged by means of plugs 21 and O-rings 23 such that the plugs are flush with the inner surface of body 15, thereby preventing voids adjacent the plugs. The adjuster assembly 12, including activator assembly 25 and inlet flit 26, are moved upwardly, as described hereinafter, so as to be above the packing ports 18. A slurry of packing medium is pumped into body 15 through the packing ports 18 to form the bed of medium 24. After the packing medium is pumped into the body 15, the adjuster assembly 12 activator assembly 25 and inlet frit 26 are lowered down onto the bed of medium past the packing ports 18 and the ports 18 are then plugged with plug 20 and O-ring 22. The height and/or compression of the bed of medium 24 is determined by the adjustment of the adjuster assembly 12, as described hereinafter.

To unpack or remove the bed of medium 24, the plugs 21 in ports 19 are removed, and the adjuster assembly 12, activator assembly 25, and inlet frit 26 are raised above the packing ports 18. The plugs 20 in ports 18 are removed and a buffer material is pumped through the packing ports 18 to liquefy the bed of medium 24, which is then drawn out through the unpacking ports 19. The body 15 is thereafter flushed out, if needed, and the ports 19 are plugged again and a slurry of fresh medium is pumped into body 15 through packing ports 18, and the adjuster assembly, as described earlier, is lowered to establish a desired height of the bed of medium.

Frits 26 and 27 are lens-shaped, each being convex or tapered on the inlet side 28 and the outlet side 29, as seen in FIG. 2, with the opposite sides of the frits 26 and 27 which are adjacent to the medium 24 being flat. This convex (thicker in the center) configuration of the inlet and outlet frits provides a unique flow focusing arrangement which promotes even sample distribution through the bed of medium 24 and reduces the uneven parabolic sample profile normally encountered in conventional axial-flow columns. In addition, the flat side of the frits support the chromatography matrix and permit even column packing.

Outlet head assembly 13 comprises a member 30 with a plurality of through openings or holes 31, only one being shown, about the periphery thereof and aligned with openings or holes 32 in flange 17, and through which bolts 33 extend to secure member 30 to flange 17, as seen in FIG. 2.

Member 30 of outlet head 13 includes an inner cut-away section of two different cross-sections forming a shoulder 34 and having a sloping or tapering surface 35 and a central opening or outlet 36 which terminates in a threaded opening 37 adapted to be connected to a tube or other collection means, not shown. A seal 38 extends around the periphery of outlet frit 27 and is secured at shoulder 34 between member 30 and a lower end of the body 15 and an inner section of flange 17, and is flush with the inner surface of body 15, thereby preventing a void which could promote sample component mixing. The details of seal 38 are shown more clearly in the enlarged view thereof in FIG. 8.

Top head assembly 11 comprises a cover plate or member 39 having a peripheral flange 40 with a tapered outer section, and which abuts with flange 16 of body assembly 10 and around which band clamp 14 is mounted. Cover plate 39 is provided with a kidney-shaped opening or clean-out port 41 which allows ready access to a space or area 42 between cover plate 39 and seal activator assembly 25. A port cover or member 43 (see FIG. 1) having a cutaway section 44 is rotatably mounted on cover plate 39 to cover and uncover the clean-out port 41 as indicated by the direction arrow 45. Port cover 43 has been omitted from FIG. 2. The clean-out port 41 allows removal of any packing buffer solution from the space 42 by aspirating it out, when cutaway section 44 of port cover or member 43 is aligned therewith, and is covered by member 43 to keep out foreign objects.

Adjuster assembly 12 is mounted to cover plate 39 of top head assembly 11 by means of a member 46 and bolts 47, with member 46 including a cutaway section 48, as seen in FIG. 2 and shown in greater detail in FIG. 3B. Cover plate 39 includes a central opening 49 and an upwardly protruding section 50 through which adjuster assembly 12 extends. FIG. 1 illustrates the external components of adjuster assembly 12, while FIGS. 2–8 illustrate various internal components of assembly 12. As shown in FIGS. 1 and 2, the adjuster assembly 12, in addition to seal/frit activator assembly 25, comprises an adjuster tube assembly generally indicated at 51 and a split-nut actuator assembly, generally indicated at 52, which are mounted in and extend through the central opening 49 of cover plate 39. The assemblies 25, 51 and 52 are seen in enlarged views in FIGS. 3A–3C.

The adjuster tube assembly 51 comprises three (3) concentric tubes, an inner sample inlet tube 53, a push tube 54 for adjusting an inlet seal 55 of the seal/frit activator assembly 25 described in detail hereinafter, and an adjustment tube 56 which is threaded externally at 57 and cooperates with the split-nut actuator assembly 52 and with the seal/frit activator assembly 25, described in detail hereinafter. A seal adjustment handle or knob 58 having an opening 59 therethrough is secured to the outer end of a short threaded tube 54' which abuts the outer end of push tube 54, extends around the outer end of adjustment tube 56, with inlet tube 53 extending through opening 59 therein. Tube 56 is provided with internal threads at the upper end which cooperate with the threads on tube 54'.

Sample inlet tube 53 has a central opening 60 therein. The tube extends the full length of adjusted assembly 12, and is secured at the inner end thereof, in a central opening 61 of an inlet plate 62 of assembly 25. Inlet plate 62 includes a concave face section 63 and has inlet seal 55 and an inlet frit retainer 64 secured to the periphery thereof (see FIGS. 4A–4B). Upper frit 26 is retained about the periphery thereof by retainer 64 and is spaced from face section 63 of inlet plate 61 to define a sample inlet area or region 65 therebetween (see FIG. 3C). The outer end of sample inlet tube 53 is provided with a reduced diameter section 66 for fluid coupling. The adjuster assembly 12 can be grasped by means of handle or knob 58 to remove same and top head assembly 11 from body assembly 10 when the quick release band clamp 14 is removed or released from around flanges 16 and 40.

The seal/frit activator assembly 25 includes, in addition to inlet tube 53, inlet plate 62, seal 55 and frit retainer 64, a seal activator or adjuster member 67 having a central opening 68 through which tubes 53 and 56 extend, and in which push tube 54 terminates (see FIG. 3C). Member 67 includes a peripheral flange section 69 which is constructed to provide a friction or snap-fit around inlet plate and in abutment with seal 55. In addition, member 67 is provided with an annular groove 70 adjacent central opening 68 in which is located a seal 71, such as an O-ring, an annular cutaway 72, and a plurality of horizontally extending passages or opening 73, only one being shown, positioned in spaced relation thereabouts. A plate 74 secured to the inner end of adjustment tube 56, such as by welding, is connected to inlet plate 62 by a plurality of bolts 75, the heads of which are located in cutaway 72 of adjuster member 67. Inlet plate 62 is provided with a peripheral groove 76 in which is located a seal 77, such as an O-ring to prevent leakage between inlet plate 62 and flange section 69 of member 67.

Adjustment tube 56 is provided with a plurality of openings 78 which align with horizontal passages 73 in member 67. Push tube 54 is provided with a plurality of longitudinally extending key slots 79 at the inner end thereof and which align with openings 78 in adjustment tube 56. Mounted in horizontal passages are pins 80, each of pins 80 having a reduced diameter end 81 which extends through openings 78 and into key slots 79. While only one of pins 80 is illustrated, at least three (3) such pins with accompanying passages 73, openings 78 and slots 79 are spaced around the seal adjuster member 67 and around the adjustment tube 56 and push tube 54. As the handle 58 is rotated in a clock-wise direction, push tube 54 is forced down contacting pin heads 81, which through pins 80 force adjuster member 67 downward. With the adjustment tube 56 fastened to inlet plate 62 by plate 74 and split-nuts and bolts 75, seal adjuster member 67 and inlet plate 62 are brought together forcing seal 55 against the inner wall of cylindrical body 15. Thus, as seen in FIGS. 4A and 4B, by clockwise rotation of handle 58 the seal 55 is moved from its non-sealing position with respect to the wall of body 15, as shown in FIG. 4A, to its sealing position against the wall of body 15, as shown in FIG. 4B. To release the seal 55, the handle 58 is turned in the opposite direction (counter-clockwise) whereby push tube 54 moves upward allowing the seal adjuster member 67 and inlet plate 62 to separate which allows the seal 55 to relax away from the body 15 as shown in FIG. 4A. In the relaxed position of seal 55, as seen in FIG. 4A, there is a space 82 between adjuster member 67 and inlet plate 62, and a space 83 between seal 55 and body 15, with spaces 82 and 83 being eliminated when the seal 55 is in its non-relaxed or sealing position as seen in FIG. 4B. There are springs between inlet plate 62 and seal adjuster 67 (not shown) which push up on seal adjuster 67 and the pins 80 and thereby on push tube 54.

In addition to its function relative to movement of seal 55, the seal/frit activator assembly 25 functions as a medium bed height adjuster by movement of the split-nut actuator assembly 52 which includes adjustment tube 56. When the actuator assembly 52, structural details of which are described hereinafter, is in its locked or engaged position, the seal/frit activator assembly 25 can be moved up or down by rotation of a handle 84 secured to actuator assembly 52 by means of bolts 85 which extend through split-nut body or housing members 86 and 87 (see FIGS. 2 and 3B). Housing members 86 and 87 may be integrated into a single member. When the actuator assembly 52 is in its unlocked or disengaged position, the seal/frit activator assembly 25 can be freely moved up or down by grasping the handle 58 whereby the tube assembly 51 and assembly 25 attached thereto through adjustment tube 56 can be raised or lowered.

The components of split-nut actuator assembly 52 are illustrated in FIGS. 1, 3B, 5A–5B, 6A–6B, and 7. As seen in FIGS. 1, 5A and 6A, the rotatable handle 84 includes a cutaway or recessed section 88 in which is located a "cam-action" lever or handle 89 and is constructed to constitute a "snap-action" type lever as a result of the cam-action produced by flat end 90 and adjacent curved surface 91 thereof. The lever 89 is connected to a pin, rod means or arm 92 by a pin 93, with rod 92 means extending through an opening 94 in recessed section 88 of handle 84 and connected to a slider assembly generally indicated at 95 and into a spring assembly generally indicated at 96. The details of the slider assembly 95 and spring assembly 96 are shown in FIGS. 5A and 6A, and constitute part of a locking mechanism for adjustment tube 56. Note that FIG. 5A illustrates the components of assembles 95 and 96 in the locked or operational position, where lever 89 is horizontal in handle recessed section 88, and FIG. 6A illustrates these components in the unlocked or non-operational position, where lever 89 is vertical in recessed section 88. Thus, as will be seen hereinafter, when the lever 89 is raised (vertical), the locking mechanism, which includes the assembles 95 and 96 and split-nut actuator assembly 52 (see FIGS. 2, 3B, 5B, 6B and 7), described in detail below, is released from contact with the threads 57 of adjustment tube 56, and tube assembly 51 and seal/frit activator assembly 25 can be moved upwardly without removal of the top head assembly 11 so that the bed of medium 24 can be easily packed or unpacked.

The split-nut actuator assembly 52, slider assembly 95 and spring assembly 96 are located within the split housing comprising members 86 and 87, with rod 92 extending through an opening 96 in upper housing member 86. Lower housing member 87 is provided with an opening 98 in which spring assembly 96 is located. Bushings 86' and 87' are provided intermediate housing members 86–87 and cover plate 39 and handle 84 to transfer the force on the split nut via the adjuster to the top head, as seen in FIGS. 2 and 3B.

The components of slider assembly 95 and split-nut actuator assembly 52 interact to produce the above described locking-unlocking mechanism for adjustment tube 56, and therefore the components of these assembles will be described hereinafter as being one assembly. The pin or rod means 92 connected at one end via pin 93 to lever 89 is connected at the opposite end to or integral with a member 99 (FIGS. 5A–6A) having a pair of slots 100 (FIGS. 5B–6B), and a split-nut assembly composed of members or sections 101 and 102 are slidable, supported to member 99 via pins 103 and 104, respectively, located in slots 100 of member 99. Split-nut sections 101 and 102 are pivoted on a pair of pins 105 and 106, respectively, with the ends of pins 105 and 106 being secured in passages or openings 107 and 108 in upper housing member 86 (see FIGS. 5B, 6B and 7). Split-nut sections 101 and 102 each include an inner curved section 109 and 110, respectively (FIGS. 6B and 7), provided with threads 111 (FIG. 6B) which are adapted to be in contact with threads 57 on adjustment tube 56 (FIGS. 3B–5B-7), or be free from contact with threads 57 (FIG. 6B), when snap-action lever 89 is in lowered position (FIG. 5A) or in raised position (FIG. 6A), due to pins 112, interconnecting member 99 and split-nut sections 101 and 102, as seen in FIGS. 5A, 6A and 7. When split-nut sections 101 and 102 are in contact with threads 57 of adjustment tube 56, as shown in FIGS. 2, 3B, 5A–5B and 7), rotation of handle 84 moves the tube assembly 51 and seal/frit assembly 25 up or down depending on the direction of rotation of handle 84. When split-nut sections 101 and 102 are not in contact with threads 57 of adjustment tube 56, as shown in FIGS. 6A–6B, the assemblies 51 and 25 can be raised or lowered freely by grasping section 66 of inlet tube 53. Thus, movement of snap-action lever 89 provides for a rapid or rough height adjustment of assembly 25 above medium 24 in cylindrical body 15, or provides for a slow or fine height adjustment of assembly 25.

Spring assembly 96 functions to control the movement of lever 89 and combined assemblies 95 and 52, and comprises a nut 113 having a washer 114 located in opening 98 of lower housing member 87 and secured in member 99, as seen in FIGS. 5A and 6A. A first spring 115 (or a spacer) is located around bolt 113 and intermediate washer 114 and member 99, while a second spring 116 is located around spring 115 and intermediate washer 114 and a protruding shoulder 117 on housing member 87 which extends into opening 98. Spring 115 is of a greater strength (heavier) than spring 116 as illustrated by the relative diameters of the coils thereof.

While the pin 92 or rod means and bolt 113 of the slider and spring assemblies 95 and 96 have been described as being separate components and secured to slider member or block 99, it may be preferred to utilize a single pin 92 with a first reduced diameter section forming a first shoulder and a second reduced diameter section which is threaded, and the member 99 provided with an opening therethrough and into which the first reduced diameter section of pin 92 is located. Thus, a nut and the washer 114 would secure spring 115 around the threaded section of the pin 92 against the lower end of member 99, as shown, with the member 99 abutting against the first shoulder of pin 92.

As seen in FIG. 5A, when the snap-action lever 89 is lowered, the spring 115 is stretched, the spring 116 is compressed, and the member 99 and associated split-nut sections 101 and 102 are moved upwardly whereby these sections pivot on pins 105 and 106 and contact the threads 57 on adjustment tube 56 as shown in FIG. 5B. Upon upward movement of the lever 89, as seen in FIG. 6A, the springs 115 and 116 produce a downward movement on member 99 causing split-nut sections 101 and 102 to pivot outwardly to their non-contact or release position shown in FIG. 6B. Thus, due to the spring assembly 96, movement of the lever 89 produces a snap action for quick release of the split-nut actuator assembly 52 from around the tube assembly 51.

Referring now to FIG. 8, the lower or output frit 27 is secured by output seal 38 which consists of a horizontal section 118 and a reversed L-shaped section 119, such that the periphery of frit 27 is located within a slot formed by seal sections 118 and 119 thereby preventing any leakage of fluids. An outer edge portion of horizontal seal section 118 is located in a cutaway 120 in member 30 of outlet head assembly 13 forming a shoulder 121, and the seal section 118 is retained between shoulder 121, flange 17 and the end of cylindrical body 15. Note that with the construction of seal 38 no voids are formed between the body 15 and the outlet flit 27.

FIG. 9 is an embodiment of the improved chromatography column of the present invention for smaller volume or preparative applications than large volume or preparative applications for which the column of FIGS. 1–8 is designed. Many of the components of the FIG. 9 embodiment are generally similar to components of the FIGS. 1–8 embodiment, and identical or similar components will be given corresponding reference numerals. The column of FIG. 9 basically comprises a body or housing assembly 10', a top head assembly 11', an adjuster assembly 12', and an outlet head assembly 13'. Top head assembly 11' is removably connected to body assembly 10' via a quick release band clamp assembly 14'.

Body or housing assembly 10' comprises a cylindrical member or body 15' with an upper flange 16' and a lower flange 17' secured to or made integral with body 15'. Cylindrical body 15' and flange 17' may be provided with packing and unpacking ports and removable plugs therefor, as in FIG. 1 embodiment. Also, as in FIG. 1, upon release of the band clamp assembly 14' the top head assembly 11' and adjuster assembly 12' can be lifted from body 15' to enable packing or unpacking a bed of separation medium 24' if no packing and unpacking ports are provided. Like the FIG. 1 embodiment, FIG. 9 includes a seal/frit activator assembly 25' having an inlet frit 26' located at the lower end thereof. The details of the activator assembly 25' will be described hereinafter.

An outlet frit 27' is located in outlet assembly 13' which comprises a member 30' having openings 31' which align with openings 32 in flange 17', and through which bolts 33 extend to secure member 30' to flange 17'. Member 30' includes an inner cutaway section 34' having a tapering surface 35' and a central outlet 36'. A seal 38' extends around the periphery of outlet frit 27' and is secured in cutaway 34' by flange 17'. Frits 26' and 27' may include the convex surfaces of the frits in the FIG. 1 embodiment, if desired, and the seal 38' can be replaced with an output seal of similar construction to that of the FIG. 1 column.

Top head assembly 11' comprises a cover plate 39' having a flange 40' which abuts with flange 16' and around which band clamp assembly 14' is positioned. Cover plate 39' is provided with an opening or clean out port 41' which allows ready access to a space or area 42' between cover plate 39' and activator assembly 25' for cleaning thereof. If desired, a port cover may be mounted on cover plate 39' to cover the clean out port 41', as in the FIG. 1 embodiment.

Adjuster assembly 12' is mounted on cover plate 39' via a hollow member or sleeve 120 which includes a tapered lower section 121 and a flat outwardly extending flange 122 having an aperture 123 therein. A plate 124 having an aperture 125 therein is secured to flange 122 and cover plate 39' by bolts 126, only one being shown, which is screwed into a threaded opening 127 in cover plate 39'. A hollow member or collet 128 having a tapered lower section 129 and a threaded upper end section 130 is positioned within sleeve 120 and supported by plate 124. The tapered section 129 of collet 128 is in contact with tapered section 121 of sleeve 120. An adjustment nut or knob 131 having a threaded opening 132 is threaded onto section 130 of collet 128 and abuts the upper end of sleeve 120. Thus, rotation of knob 131 causes collet 128 to be raised or lowered for reasons described hereinafter.

The adjuster assembly 12' also includes the seal/frit activator assembly 25' located within body 15' and an adjuster tube assembly 51' which extends through collet 128 and is attached to activator assembly 25'. The adjuster tube assembly 51' includes three (3) concentric tubes, an inner sample inlet tube 53', a push tube 54' positioned around tube 53' for activating the assembly 25', and an adjustment or pull tube 56' positioned around push tube 54' and provided at the upper end thereof with threads 133. A push tube adjustment handle or knob 58' having an opening 134 and an enlarged threaded opening or countersink 135 extends around inlet tube 53' and is threaded onto threads 133 of adjustment tube 56', such that the area of knob 58' between opening 134 and threaded opening 135 contacts the outer end of push tube 54'. Thus, rotation of knob 58' on threads 133 causes push tube 54' to move downward and the pull or adjustment tube 56' to move upward, or vice versa for positioning an inlet seal 55' of the seal/frit activator assembly 25', as described hereinafter. Adjustment tube 56' is stationary and push tube 54' is pushed down as a result of collet 128 holding the adjustment tube 56'.

Sample inlet tube 53' has a central longitudinally extending opening 60' and is secured at the lower or inner end thereof in a central opening 61' in an inlet plate 62' of assembly 25'. Inlet plate 62' includes a concave face section 63' and has the inlet seal 55' and the inlet frit 26' mounted on the periphery thereof, with the frit 26' spaced from face 63' of inlet plate 61' to define a sample inlet area or region 65' therebetween.

The seal/frit activator assembly 25' includes, in addition to inlet tube 53', seal 55', frit 26' and inlet plate 62', a seal activator or adjuster member 67', having a central opening 68' and which includes an outer flange section 69'. Flange section 69' is constructed to provide a friction or snap-fit around inlet plate 62' and is in abutment with seal 55'. In addition, member 67' is provided with an annular groove 70' adjacent central opening 68' in which is located a seal 71', such as an O-ring, and a plurality of horizontally extending passages 73', only one being shown, positioned in spaced relation thereabouts. The pull or adjustment tube 56' is provided at the lower end with a flat flange 136 having openings 137 therein through which a plurality of bolts 75' extend into threaded openings 138 in inlet plate 62' for securing flange 136 to the inlet plate. Inlet plate 62' is provided with a peripheral groove 76' in which is located a seal 77', such as an O-ring. An opening or passage 139 extends through flange 69' to provide an access to allow a wash solution to be forced into the space above the seal for cleaning the space thereabove. The wash solution can be continually aspirated out of passage 139 or allowed to puddle and then be aspirated out when region 42' is cleaned via opening 41', as described in the FIG. 1 embodiment.

The pull or adjustment tube 56' is provided with a plurality of openings 78', only one being shown, which align with horizontal passages 73' in adjuster member 67'. Push tube 54' is provided with a corresponding number of longitudinally extending key slots 79' at the inner end thereof and which align with openings 78' in adjustment tube 56'. Mounted in horizontal passages 73' are a plurality (only one being shown) of pins 80' having a reduced diameter end sections 81' which extend through openings 78' and into key slots 79'. As the handle or knob 58' is rotated in a clock-wise direction, adjustment tube 56' is raised and at the same time the push tube 54' is forced downward contacting pin end sections 81' which through pins 80' forces adjuster member 67' downward. With the adjustment tube 56' secured to inlet plate 62' via flange 136 and bolts 75', the seal adjuster member 67' and inlet plate 62' are brought together compressing and forcing seal 55' outward against the inner wall of cylindrical body 15', as described earlier with respect to FIGS. 4A and 4B illustrating the seal 55 of the FIG. 1 embodiment. To release the seal 55', the handle 58' is turned in the opposite direction whereby push tube 54 is allowed to move upward as described earlier with respect to the FIG. 1 embodiment. The seal 55' may be of a triangular or V-shape as in the FIG. 1 embodiment. Springs (not shown) between inlet plate 62' and adjuster member 67' assist the transfer of force on the split nut via the adjuster to the top head.

The method for adjusting the bed height of medium 24' involves the use of the collet 128 and adjuster nut or knob 131. When knob 131 is turned to tighten or loosen the collet 128 via movement of tapered surface or section 129 with respect to tapered surface or section 121 of sleeve 120, adjustment tube 56' is gripped or released, whereby the adjustment tube, the assembly 25', and upper frit 26' can be raised or lowered manually when the collet 128 is released (not gripping) tube 56'. It is intended that the height of the bed of medium 24' is adjusted prior to compressing the seal 55' against the body 15' to prevent strain and other adverse effects on the seal. The collet 128 can be used, instead of the split-nut of the FIG. 1 embodiment, as a locking mechanism for the adjustment tube 56', for small columns where it is easy to lift or lower the adjuster tube 56' manually.

It has thus been shown that the improved chromatography column of the present invention provides for easy adjustment of the media bed via the locking mechanism, uniform flow of the sample by means of the configuration of the frits, and ready access to the interior for cleaning and sanitation purposes via the construction of the top cover and a quick-release band, and elimination of voids via the construction of the seals.

By way of example, the column body may be constructed from acrylic materials having a length of 20–100 cm and inner diameter of 10–40 cm; the inlet or top assembly and the outlet head may be constructed of polypropylene; the seals constructed of silicone or other suitable types of rubber; the frits constructed of porous polyethylene; the adjuster handles constructed of polyurethane or glass; and the metallic hardware, such as the components of the slider and spring assemblies and the collet, made of 316 stainless steel.

The foregoing description of the preferred embodiments, materials, parameters, and the like of the subject invention have been presented for purposes of illustration and description and for a better understanding of the invention. It is not intended to be exhaustive or to limit the invention to the precise form disclosed; and, obviously, many modifications and variations are possible in the light of the above teaching. The particular embodiments were chosen and described in some detail to best explain the principles of the invention and its practical application thereby to enable others skilled in the relevant art to best utilize the invention in various embodiments and with various modifications as are suited to the particular use contemplated. It is intended that the invention be defined by the claims appended hereto.

What is claimed is:

1. An axial flow chromatography column, comprising:

a housing having flanges at both ends and operatively connected to an outlet head assembly at one end which includes a central opening and a tapering upper surface and an adjuster assembly at the other;

a pair of bed support frits located within said housing and adapted to retain a bed of chromatographic medium therebetween and wherein said pair of frits each has one side having a convex configuration, said convex configured sides being located oppositely with respect to an associated bed of chromatography medium;

a pair of seal means located within said outlet head assembly and constructed so as to retain a peripheral edge of one of said frits and wherein said pair of seal means consists of a horizontal section and a reversed L-shaped section, with said peripheral edge of said one frit being located within said reversed L-shaped section;

a top assembly adapted to be removably connected to said housing;

means for removably connecting said top assembly to said housing flange;

a bed adjuster assembly located in said housing and said top assembly;

a locking mechanism mounted in said top assembly for releaseably retaining said bed adjuster assembly, such that release of said locking mechanism enables rapid height adjustments of said bed adjuster assembly; and means for making fine height adjustments of said bed adjuster assembly.

2. The column of claim 1, wherein said bed adjuster assembly includes a hollow member provided with a plurality of external threads on at least a section thereof via which said locking mechanism releasably retains said bed adjuster assembly.

3. The column of claim 2, wherein said locking mechanism includes a movable member having a threaded section and a tapered section which is positioned in contact with said threads of said hollow member and means for moving said movable member for retaining and releasing said bed adjuster assembly.

4. The column of claim 3, wherein said movable member comprises a collet, and wherein said tapered section is in contact with a tapered section of a sleeve mounted in said top assembly, whereby movement of said means for moving said movable member causes movement between said tapered sections.

5. The column of claim 2, wherein said locking mechanism includes a plurality of movable members, each having a threaded section which is removably positioned in contact with said threads of said hollow member, and means for moving said plurality of movable members for retaining and releasing said bed adjuster assembly.

6. The column of claim 5, wherein said locking mechanism includes a lever having a cam-like surface thereon, a spring biased rod means operatively connected to said lever, and means for connecting said spring biased means to said plurality of movable members.

7. The column of claim 6, wherein said plurality of movable members are pivotably mounted, wherein said connecting means includes a member having a plurality of slots therein and a plurality of pins in said slots so as to be movably connected to said spring biased rod means, such that movement of said rod means by said lever causes said threads on said plurality of movable members to engage or disengage said threads on said hollow member of said bed adjuster assembly.

8. The column of claim 3, wherein said lever is operatively mounted on said means for making free height of said bed adjuster assembly.

9. The column of claim 1, further comprising means for making free height adjustments of said bed adjuster assembly comprising a rotatable handle, said locking mechanism being operatively mounted to said rotatable handle.

10. The column of claim 1, wherein said means for removably connecting said top assembly to said housing flange comprises a quick-release band assembly.

11. In a chromatography column having a housing containing a bed of chromatography media and a top assembly, the improvement comprising:

an adjustable bed assembly including a plurality of hollow members;

a rotatable handle operatively mounted on said top assembly and operatively connected to at least one of said hollow members for adjusting said adjustable bed assembly;

and a locking mechanism operatively connected to said rotatable handle and releasably connected to said adjustable bed assembly, wherein said locking mechanism includes a lever having a cam surface operatively mounted to said rotatable handle; a rod menas operatively connected to said lever; a spring assembly operatively connected to said rod means; and an actuator assembly operatively connected to said rod means and to one of said hollow members of said adjustable bed assembly whereby movement of said level in one direction causes said actuator assembly to contact said one hollow member and movement of said lever in an opposite direction causes said actuator assembly to withdraw contact with said one hollow member.

12. The improvement of claim 11, wherein said actuator assembly includes a plurality of movable members having threads on one portion of each member, and wherein said one hollow member is provided with a plurality of threads adapted to cooperate with said threads on said plurality of movable members, whereby said plurality of movable members are moved by said lever to cause said threads thereon to contact threads on said one hollow member or release contact between the threads of said movable members and said one hollow member.

13. The improvement of claim 12, wherein said adjustable bed assembly also includes a member which extends around and is adjacent to the interior of said housing and is provided with a groove about the periphery thereof, and wherein said groove retains a seal in contact with an interior surface of said housing.

14. The improvement of claim 13, additionally including a pair of spaced bed support frits, each of said frits having a convex surface on one side thereof to provide for oven distribution of a sample flow through the bed which is located between said frits, one of said frits being retained by said member of said adjustable bed assembly.

15. The improvement of claim 11, wherein said plurality of hollow members comprises a plurality of concentric tubes, an outer tube of said concentric tubes constituting said one hollow member, said outer tube being provided with external threads on at least a portion thereof and a plurality of apertures in one section thereof;

an inner tube of said concentric tubes comprises a sample inlet tube and is connected at an inner end to an inlet plate of said adjustable bed assembly;

said inlet plate being constructed to retain a seal and an inlet frit at the periphery thereof, said outer tube being connected to said inlet plate, said adjustable bed assembly additionally including an adjuster member having a central opening and a plurality of horizontal passages therein and connected to said inlet plate, said concentric tubes extending into or through said central opening, an intermediate tube of said concentric tubes is provided at an inner end thereof with a plurality of longitudinally extending slots, a plurality of pins positioned in said horizontal passages in said adjuster member and extending through said apertures in said outer tube and into said slots in said said outer tube being connected to means via said external threads for moving same in opposite directions, said means being constructed to cooperate with said intermediate tube for moving same, whereby movement of said means for moving causes movement oil said outer and intermediate tubes thereby contacting said plurality oil pins causing movement of said adjuster member and said inner plate, and whereby said adjustable bed assembly can be raised or lowered in said housing said column.

16. The improvement of claim 15, wherein movement of said means for moving produces opposite movement of said outer and intermediate tubes causing said adjuster member and said inlet plate to move in opposite directions forcing said seal retained at the periphery of said inlet plate against an inner surface of said housing.

17. The improvement of claim 16, wherein said locking mechanism includes a collet mounted in said top assembly of said column.

18. The improvement of claim 16, wherein said locking mechanism includes pivoted members constructed to contact said outer tube.

19. The improvement of claim 18, wherein said locking mechanism also includes a snap-action lever means operatively connected to said pivoted members.

20. The improvement of claim 11, additionally including at least one aperture in said top assembly to allow for cleaning of a portion of said housing without removing said adjustable bed assembly.

21. The improvement of claim 20, wherein said adjustable bed assembly is provided with at least one opening therein for cleaning portions thereof.

22. The improvement of claim 11, additionally including inlet and outlet seal assemblies constructed and positioned in said housing so as to prevent voids therein.

23. The improvement of claim 22, wherein said inlet seal assembly includes a seal having a V-shaped configuration, and wherein said outlet seal assembly includes a seal having a horizontal section and a reversed L-section.

24. The improvement of claim 11, additionally including packing and unpacking ports located in said housing, said ports being provided with removable plug means.

* * * * *